United States Patent [19]

Morishita et al.

[11] 4,135,943
[45] Jan. 23, 1979

[54] NOVEL SELECTIVE ADSORBENTS

[75] Inventors: Masataka Morishita; Mitsuru Fukushima; Yoshihito Inaba, all of Shizuoka, Japan

[73] Assignee: Toyo Jozo Company, Ltd., Japan

[21] Appl. No.: 673,522

[22] Filed: Apr. 5, 1976

Related U.S. Application Data

[63] Continuation of Ser. No. 475,174, May 31, 1974, abandoned.

[30] Foreign Application Priority Data

Jun. 13, 1973 [JP] Japan .................................. 48-67053
Jan. 22, 1974 [JP] Japan .................................. 49-9855
May 31, 1975 [JP] Japan .................................. 50-61468

[51] Int. Cl.$^2$ .......................... C08L 5/00; B01J 31/06
[52] U.S. Cl. .................................... 106/209; 252/428; 260/17.4 ST; 260/17.4 UC; 260/29.6 R; 260/42.53
[58] Field of Search ................. 106/209; 252/426, 428

[56] References Cited

U.S. PATENT DOCUMENTS

| | | | |
|---|---|---|---|
| 2,816,087 | 12/1957 | Coover | 260/29.6 B |
| 3,442,819 | 5/1969 | Herbert | 252/428 |
| 3,941,718 | 3/1976 | Barabas | 252/430 |

*Primary Examiner*—Theodore Morris
*Attorney, Agent, or Firm*—Craig & Antonelli

[57] ABSTRACT

Selective adsorbents are prepared by dispersing powdery adsorbents in a composition for forming a crosslinked high molecular weight polymer, then dispersing in fine droplets the dispersion in a vehicle and performing crosslinking reaction to form a crosslinked polymer. The fine powders of adsorbents are enclosed within the crosslinked polymer and dispersed in three-dimensional spaces. Hydroxyl group containing polymeric substance and crosslinking agent or a monomer mixture of ethylenically unsaturated monomer and crosslinking monomer is used in said composition. The selective adsorbents can be useful in separation or purification of various organic compounds.

30 Claims, No Drawings

NOVEL SELECTIVE ADSORBENTS

This is a continuation of application Ser. No. 475,174 filed May 31, 1974, now abandoned.

This invention relates to novel selective adsorbents containing powdery adsorbents dispersed in three-dimensional spaces in crosslinked high molecular weight polymers and a process for producing the same.

Heretofore, there have been known substances having molecular sieving effect. One is hydroxyl group containing polymeric substance which is obtained by crosslinking polysaccharide. The other is a crosslinked polymer obtained by polymerizing ethylenically unsaturated monomers in the presence of crosslinking agents. However, molecular sieving effect of these polymers is such that they separate one substance from others by the difference in retention time through the molecular sieving polymers. Accordingly, a good deal of molecular sieving polymers is required for separation of a small amount of the substances to be treated. Furthermore, because they have no adsorption ability, molecular sieving operation is performed only chromatographically, namely, by the method wherein a solution of the substances to be treated is flown linearly in one direction. In such a method, no continuous operation is possible. For effective separation by this method, molecular sieving polymers should be packed in thick layers in a column and it takes a long time before molecular sieving is effected. Hence, these molecular sieving polymers are not suitable for industrially large scale applications.

An object of the present invention is to provide a selective adsorbent which can perform molecular sieving of the substances to be treated in a manner such that substances having smaller molecular sizes can be separated clearly from those having larger molecular sizes by selective adsorption of the former.

Another object of the present invention is to provide a process for producing a selective adsorbent as mentioned above.

Still another object of the present invention is to provide a process for separation of organic compounds, which comprises contacting a mixture of adsorptive organic compounds and non-adsorptive compounds with the aforesaid selective adsorbent.

It has now been found that a selective adsorbent, containing powdery adsorbents enclosed within crosslinked high molecular weight polymer and dispersed in three-dimensional space therein, can perform molecular sieving actively as mentioned above and with a very small amount. It has further been found that molecular sieving may be performed favorably either in batch system or in column system.

According to the present invention, there is also provided a process for preparing a selective adsorbent which comprises first dispersing powdery adsorbents in a composition for forming a crosslinked high molecular weight polymer, then dispersing in fine droplets the dispersion in a vehicle and effecting formation of a crosslinked high molecular weight polymer, thereby forming selective adsorbents shaped in spherical particles containing said powdery adsorbents enclosed within said crosslinked polymer and dispersed in three-dimensional spaces therein.

The powdery adsorbents used as starting materials in the present invention are not limited, so long as they have adsorption ability. Typically, they include powders of activated charcoal, bone black, alumina, silica gel zeolite, bentonite, calcium phosphate gel, ion-exchange resin, chelate resin and so forth.

According to one preferred embodiment of the process of the present invention (method A), a polymeric substance containing hydroxyl groups and a crosslinking agent therefor are used in the composition for forming a crosslinked high molecular weight polymer. According to another preferred embodiment of the process of the present invention (method B), a monomeric mixture containing an ethylenically unsaturated monomer and a polyfunctional crosslinking monomer is used as the composition for forming a crosslinked high molecular weight polymer.

In the following, each preferred embodiment is explained in detail.

I. Method A

According to this method, a polymeric substance containing hydroxyl groups is used as one component of the composition. Examples of such polymeric substances are polysaccharides such as dextrin, dextran, starch, agar, agarose, cellulose or polyglucose. There may also be used derivatives of said polysaccharides such as methyl dextran, ethyl dextran, hydroxypropyl dextran, methyl cellulose or ehtylhydroxyethyl cellulose, or products obtained by partial depolymerization of the same, as well as, fractions thereof, sugar alcohols such as sorbitol and polyvinyl alcohols. These polymeric substances are dissolved in a basic solvent containing basic substances. Any basic substance may be used so long as it can exhibit basic property in a solution. Alkali metal hydroxide such as sodium hydroxide is most suitable. Alternatively, other substances such as quaternary ammonium compounds, alkali metal carbonates, alkali earth metal carbonates or alkali earth metal hydroxide may also be useable.

As crosslinking agents, polyfunctional compounds reactive with hydroxyl groups in the above polymeric substance are used. For example, there may be used epichlorohydrin, dichlorohydrin, 1,2-3,4-diepoxy butane, bis-epoxy-propylether, ethylene glycol-bis-epoxy-propyl ether, 1,4-butane-diol-bis-epoxy-propyl ether and the like.

As a vehicle to be used in this method, there may be used a fluid which is immiscible with water, not reactive with the aforesaid crosslinking agents but can dissolve said crosslinking agents, and can form W/O emulsion droplets. For example, there are organic solvents, inclusive of aliphatic hydrocarbons such as hexane or heptane, cycloaliphatic hydrocarbons such as cyclohexane or cycloheptane, aromatic hydrocarbons such as benzene, toluene or xylene, halogenated hydrocarbons such as chloroform, carbon tetrachloride, dichloromethylene or dichloroethylene, and halogenated aromatic hydrocarbons such as dichlorobenzene or chlorobenzene. There may also be used solutions dissolved in these solvents, containing 0.1 to 15% polyvinyl acetate, acetyl cellulose, acetyl butyl cellulose or ethylenevinyl acetate copolymer. Fluid paraffins and silicone oils may also be used as vehicle.

If necessary, there may also be added surfactants soluble in the above vehicles and low in HLB value. Examples of such surfactants are alkyl esters of lanolin derivatives, glycerine, ethylene glycol or propylene glycol, sorbitane alkyl esters, polyoxyethylene sorbitane alkyl esters, polyoxyethylene alkyl ethers, polyoxyethylene alkyl esters, polyoxyethylene-polyoxypropylene copolymers, polyoxyethylene alkyl phenol derivatives, polyoxyethylene alkyl amides and polyoxyethylene glycerine alkyl esters. Alternatively, animal oils, vegetable oils or mineral oils may also be added.

In practicing the above process, a basic solution, wherein adsorbent powders are dispersed and a polymeric substance containing hydroxyl groups is dissolved, is first prepared. Fine adsorbent powders with particle sizes, for example, 0.5 to 50μ are used. The proportional amount of the powders used is preferably from 10 to 60% by weight based on the selective adsorbent obtained. The amount of the polymeric substance containing hydroxyl groups is about 30% by weight or more, preferably, 40 to 90% by weight based on the dry weight of the selective adsorbent obtained. In preparation of the basic solution, the adsorbent powders and the polymeric substance may be dispersed and dissolved, respectively, in a basic solution at the same time or in succession. Alternatively, after they are dispersed and dissolved in separate solutions, both dispersion and solution may be combined. The polymeric substance containing hydroxyl groups is preferably swelled in advance with water before it is dissolved in basic solution.

The solution thus prepared is then dispersed under stirring into a vehicle. The amount of vehicle used is about 3 times or more as much as the amount of said solution. A polyfunctional crosslinking agent reactive with hydroxyl groups of said polymeric substance is also added to the dispersion to effect crosslinking reaction. The relative amount of the crosslinking agent to said polymeric substance is ⅛ or more in weight, usually ⅛ to ¼. Thus by addition of a crosslinking agent to said dispersion, said polymeric substance reacts with the crosslinking agent to form a selective adsorbent of a crosslinked high molecular weight polymeric gel containing adsorbent. The selective adsorbent thus formed has a structure such that adsorbent powders are favorably dispersed in three-dimensional spaces in the high molecular weight polymer gel. The adsorption sites of said powders are not sheltered in such a structure. They are then recovered, washed, and, if necessary, dried.

II. Method B

According to this method, ethylenically unsaturated monomers are polymerized and crosslinked. The ethylenically unsaturated monomers may be either hydrophilic or lipophilic. For example, there may be used such hydrophilic or lipophilic monomers as vinyl chloride, vinyl acetate, vinyl ethers (e.g. vinyl ethyl ether), allyl derivatives (e.g. allyl alcohol or allyl) amine), styrene, butadiene, acrylic acid, methacrylic acid, crotonic acid, acrylamide, N-dimethyl acrylamide, dimethylamino styrene, vinyl sulfonic acid, and so forth. Two or more of these monomers may be used in combination.

As the crosslinking agents used in this embodiment, any compound having two or more functional groups reactive with the aforesaid monomers may be used. For example, there may be used polyhydric alcohol esters of acrylic acid, methacrylic acid or crotonic acid, divinyl benzene, acrylic acid anhydride, methacrylic acid anhydride, N,N'-dimethylene-bis-acrylamide, aldehydes such as glyoxal, ketones, allyl dihalogenides, alkyl dihalogenides, disulfohalogenides or polybasic acids. Above all, N,N'-dimethylene-bis-acrylamide, divinyl benzene and glyoxal are preferred.

Either lipophilic or hydrophilic vehicle may be used in this method. Lipophilic vehicle is used when the aforesaid monomer and the crosslinking agent are hydrophilic. In this case, crosslinking reaction is performed by dissolving these components in a solvent. The solvent may be water or a mixture of hydrophilic organic solvent and water. Alternatively, it may be an aqueous solution containing water-soluble viscosity increasing substances. Examples of such substances are sodium carboxymethyl cellulose, hydroxypropyl cellulose, methyl cellulose, hydroxypropyl methyl cellulose, polyvinyl alcohol, sorbitol, maltdextrin, gelatin and gum arabic. They are added for the purpose of enclosing the adsorbent powders favorably during the crosslinking reaction. As a lipophilic vehicle, any fluid poorly miscible with water, which does not dissolve and react with the aforesaid hydrophilic monomers and cross-linking agents, may be used. Examples of such vehicles are aliphatic hydrocarbons such as hexane or heptane, cycloaliphatic hydrocarbons such as cyclohexane or cycloheptane, aromatic hydrocarbons such as benzene, toluene or xylene, halogenated hydrocarbons such as chloroform, carbon tetrachloride, dichloromethane, dichloroethane, or perchloroethylene or halogenated aromatic hydrocarbons such as dichlorobenzene or chlorobenzene; solutions of about 0.1 to 15 wt.% polyvinyl acetate, acetyl cellulose, acetyl butyl cellulose or ethylene-vinyl acetate copolymer dissolved in these solvents; liquid paraffins (or halogenated paraffins); and silicone oils such as methyl silicone oil, phenyl silicone oil or methyl phenyl silicone oil. There may also be added, if necessary, surfactants which are soluble in the aforesaid vehicles and low in HLB value. Examples of such surfactants are alkyl esters of lanolin derivatives, glycerine, ethylene glycol, or propylene glycol, sorbitane alkyl esters, polyoxyethylene sorbitane alkyl esters, polyoxyethylene alkyl ethers, polyoxyethylene alkyl esters, polyoxyethylene-polyoxypropylene copolymers, polyoxyethylene alkyl phenol derivatives, polyoxyethylene alkyl amides, or polyoxyethylene glycerine alkyl esters. Other additives which may also be added are animal oils, vegetable oils or mineral oils. When a solvent having low boiling point is used as vehicle, a closed system, for example, a reflux equipment, may be used. Preferably, however, non-volatile solvents such as fluid paraffins, silicone oils, toluene or benzene are to be used.

Hydrophilic vehicles are used when the aforesaid monomer and the crosslinking agent are lipophilic. In this case, crosslinking reaction is performed by dissolving lipophilic monomers and crosslinking agents in one or a mixture of solvents which can dissolve these substances and are poorly miscible with water. These solvents include perchloroethylene, carbon tetrachloride, benzene, toluene, chlorobenzene, dichlorobenzene, cyclohexane, amyl alcohol, iso-amyl alcohol and butyl acetate. As hydrophilic vehicles, there may be used any aqueous solution of a surfactant or a hydrophilic protective colloid which does not dissolve or react with the aforesaid lipophilic monomers and crosslinking agents, can hold stably the liquid droplets thereof, and are poorly miscible with the solvents as mentioned above. For example, an aqueous surfactant solution contains 0.01 to 5%, preferably, 0.25 to 2% anionic surfactant, for example, alkyl benzene sulfonates such as Newlex R, Newlex C-1 or Newlex paste H, alkyl ester sulfonated product of organic dibasic acids such as Lapisol B, or sodium sulfate esters of higher alcohols such as Syntolex. As an aqueous protective colloid solution, there may be used an aqueous solution containing 0.05 to 5%, preferably, 1 to 2% protective colloid, for example, sodium carboxymethyl cellulose, hydroxypropyl cellulose, methyl cellulose, hydroxypropylmethyl cellulose, polyvinyl alcohol, gelatin, gum arabic, sodium alginate, sorbitol or maltdextrin. Furthermore, these surfactants and hydrophilic protective colloids may be used in combination.

In practicing the process of this embodiment, an ethylenically unsaturated monomer and a crosslinking agent therefor are first dissolved in a solvent. The amount of the crosslinking agent relative to the ethylenically unsaturated monomer is preferably from about 0.5 to 50% by weight based on the crosslinked polymer. The concentration of the ethylenically unsaturated monomer dissolved in a solvent is ordinarily 5% by weight or more, preferably, from about 10 to 50% by weight. The concentrations of the ethylenically unsaturated monomer and the crosslinking agent therefor may be varied suitably according to the desired title selective adsorbents. Then, adsorbent powders are dispersed in the solution thus prepared. The powders are preferably those which are pulverized as fine as possible. The amount of the powders used is ordinarily 60% by weight or less, preferably from about 10 to 30% by weight based on the selective adsorbent obtained. When the adsorbent powders are used in a large amount, the selective adsorent obtained is brittle, while adsorption ability per unit weight is low when they are used in a small amount. Hence, the amount should be controlled suitably so that the selective adsorbent may be high in adsorption ability and mechanical strength. The dispersion is then emulsified in vehicle. The behicle is used in an amount enough to make the dispersion emulsified therein, usually twice or more, preferably about 3 to 5 times the amount of the dispersion. Furthermore, crosslinking reaction is performed sufficiently in this system. Conventional means may be employed for this crosslinking reaction. For example, the reaction may be carried out in the presence of a catalyst. The catalyst may be ammonium persulfate, potassium persulfate, sodium persulfate, hydrogen peroxide, benzoyl peroxide, trialkyl aluminum, or sodium chlorate. Metals such as copper, iron or tin which can exist at different stages of valency may also be used as catalyst. The reaction may also be performed by irradiation of light or radiated rays. The above catalyst may be added, as described in the following examples, directly into the solution containing the ethylenically unsaturated monomer and the crosslinking agent therefor. The crosslinking reaction may take place more or less before emulsion system is obtained, but production of selective adsorbent is hardly affected thereby. By further carrying out sufficient crosslinking reaction, there are precipitated selective adsorbents wherein adsorbent powders are dispersed in three-dimensional spaces in gelled high molecular weight polymer. These are separated by conventional solid-fluid separation methods and washed to obtain selective adsorbents containing adsorbent powders.

As mentioned above, according to the present invention, there is also provided a process for separation of organic compounds by the use of the selective adsorbents as described above. A substrate containing a mixture of adsorptive organic compounds and non-adsorptive compounds is treated by passing through the selective adsorbents which are, for example, packed in a column. Examples of the mixture of organic compounds are a solution containing dyestuffs, a solution containing proteins or enzymes or a solution containing antibiotics. Alternatively, the selective adsorbents may directly be added in a vessel containing said substrate, followed by solid-fluid separation in a conventional manner. Then, depending on the object of separation, fluid layer or selective adsorbents are collected by conventional methods. Further, useful organic compounds are collected from the fluid layer or, if desired, useful organic compounds are collected by elution from the selective adsorbents.

The selective adsorbents containing adsorbent powders dispersed in three-dimensional spaces in the high molecular weight polymer obtained in the present invention have excellent molecular sieving effect without deteriorating adsorption ability of the adsorbent powders. They may be utilized for isolation, recovery, or purification of useful adsorptive organic compounds or removal of non-adsorptive organic compounds from a system containing useful adsorptive organic compounds and non-adsorptive organic compounds. For example, isolation, recovery or purification of polymyxin or tuberactinomycin N may be performed from culture broths of antibiotics such as polymyxin or tuberactinomycin N. Caramel or other natural dyestuffs may be recovered from waste liquor of alcohol fermentation. They may also be used for removal of adsorptive organic compounds from a system containing adsorptive organic compounds and useful non-adsorptive compounds. Other applications are separation or purification of useful non-adsorptive organic compounds, for example, purification such as decoloration of high molecular weight emzyme. Further applications are separation or purification of useful adsorptive organic compounds and useful non-adsorptive organic compounds from a system containing both, for example, separation, purification or recovery of egg white lysozyme and ovalubumin from egg white. Furthermore, even when many kinds of useful adsorptive organic compounds as mentioned above or many kinds of useful adsorptive organic compounds and useless adsorptive organic compounds may coexist with each other, elution may be performed one by one by suitable selection of elution conditions. Thus the selective adsorbents can be useful in various industrial applications.

The present invention is further illustrated by the following Examples.

EXAMPLE 1

Forty (40) grams of dextran having an average molecular weight of 70,000 (produced by Seikagaku Kogyo Co., Japan) are swelled with 15 ml water and then dissolved in 75 ml 5N-aqueous sodium hydroxide solution. Into this alkali solution of dextran is dispersed homogeneously 6 g activated charcoal powders (Kyoryoku Shirasagi: trade name; Takeda Chemical Industries Co.). The activated charcoal dispersion thus prepared is dispersed in fine droplets in 500 ml of a fluid paraffin of Japanese Pharmacopoeia (19 cps. at 25° C) containing 6 g magnesium stearate and 1% Lanex (produced by CRODA NIPPON Co.) under stirring with a propeller at 350 r.p.m. Then, 25 ml epichlorohydrin is added, dropwise, into this dispersion and stirring is continued at 50° C for 2 hours until selective adsorbents containing activated charcoal dispersed in crosslinked dextran polymer gels are obtained. They are collected by filtration, washed with n-hexane, acetone, water and 1N-HCl. They are further washed with water until they are neutralized, dried on air at 40° C to obtain 50 g selective adsorbents containing activated charcoal (particle sizes: 50 to 800μ).

EXAMPLE 2

Twenty (20) grams of dextran having an average molecular weight of 10,000 are swelled with 10 ml water and dissolved in 30 ml 5N-aqueous sodium hydroxide solution. Into this solution is dispersed homogeneously 2 g activated charcoal powders (Kyoryoku Shirasagi). The resulting activated charcoal dispersion is dispersed in fine droplets into 120 ml fluid paraffin of Japanese Pharmacopoeia containing 2 g magnesium stearate and 1% Lanex under stirring with a propeller at 350 r.p.m. Into this dispersion is further added, dropwise, 10 ml epichlorohydrin, followed by stirring at 50° C for 2 hours, to obtain selective adsorbents. They are washed and dried on air similarly as in Example 1 to obtain 23 g selective adsorbents (particle sizes: 100 to 800μ).

EXAMPLE 3

Sixty (60) grams of dextrin (produced by Wako Junyaku Kogyo Co.) are swelled with 20 ml water and dissolved in 80 ml 5N-aqueous sodium hydroxide solution. Into this solution is dispersed homogeneously 6 g activated charcoal powders. The dispersion thus prepared is dispersed in fine droplets into 500 ml fluid paraffin of Japanese Pharmacopoeia containing 6 g magnesium stearate and 1% Lanex under stirring with a propeller (300 r.p.m.). Furthermore, under stirring, 30 ml epichlorohydrin is added, dropwise into the dispersion. After crosslinking reaction is performed at 50° C for 2 hours, there are obtained selective adsorbents containing activated charcoal dispersed in dextrin polymer gels. They are separated by filtration, washed thoroughly with n-hexane, acetone, water, 1N-HCl and water, in this order. Then, they are dried on air stream at 40° C to obtain 70 g selective adsorbents (particle sizes: 50 to 500μ).

EXAMPLE 4

According to the procedure similar to that in Example 3, 50 g selective adsorbents containing activated charcoal dispersed in crosslinked dextrin polymer are obtained (particle sizes: 50 to 700μ). The starting materials employed are 6 g activated charcoal, 40 g dextrin, 35 ml water, 25 ml 10N-NaOH, 400 ml fluid paraffin, 1% Lanex, 6 g magnesium stearate and 30 ml epichlorohydrin.

EXAMPLE 5

When a silicone oil (KF-96: trade name; produced by Shinetsu Kagaku Co.) is used as vehicle in place of fluid paraffin in Example 3, the procedures being otherwise followed similarly as described in said Example 3, 44 g selective adsorbents containing activated charcoal dispersed in crosslinked dextrin powders (particle sizes: 50 to 800μ). The starting materials employed are 5 g activated charcoal, 35 g dextrin, 28 ml water, 17 ml 10N-NaOH, 300 ml silicone oil, 1% Lanex, 3 g magnesium stearate and 25 ml epichlorohydrin.

EXAMPLE 6

According to the similar procedure similar to that in Example 3, except that a solution of 8 g ethylenevinyl acetate copolymer (Ulthracene-760: trade name; produced by Toyo Soda Kogyo Co.) dissolved in 200 ml toluene is used as vehicle in place of fluid paraffin, 35 g selective adsorbents are obtained (particle sizes: 50 to 750μ). The starting materials employed are 3 g activated charcoal, 30 g dextrin, 18 ml water, 15 ml 10N-NaOH, 200 ml of the aforesaid vehicle and 1% Lanex.

EXAMPLE 7

Twenty (20) grams of soluble starch are dissolved in 52 ml water and 13 ml 5N-NaOH is added to this solution. Into this solution is dispersed homogeneously 6 g activated charcoal powders (Kyoryoku Shirasagi) and then the dispersion is dispersed in fine droplets under stirring into 200 ml fluid paraffin of Japanese Pharmacopoeia containing 1% Lanex. To this dispersion is added 10 ml epichlorohydrin, dropwise. The temperature is elevated to 50° C and the reaction is performed for one and half hours to obtain selective adsorbents containing activated charcoal dispersed in crosslinked polymer gels of starch. They are separated by filtration, washed thoroughly with n-hexane, acetone, water, 1N-HCl and water, in this order, and dried on air stream at 40° C to obtain 26 g selective adsorbents containing activated charcoal (particle sizes: 100 to 1000μ).

EXAMPLE 8

Twenty (20) grams of dextrin are swelled with 5 ml of water and then dissolved in 25 ml 5N-NaOH. Into this solution is dispersed homogeneously 5 g bentonite powders (produced by Kukita Yakuhin Kogyo Co.). The dispersion is dispersed in fine droplets under stirring into 200 ml fluid paraffin of Japanese Pharmacopoeia containing 1% Lanex. Then, 20 ml epichlorohydrin is added, dropwise, into the dispersion and the temperature is elevated to 50° C to effect crosslinking reaction. The selective adsorbents obtained are separated by filtration, washed thoroughly with n-hexane, acetone and water, in this order, and dried on air stream at 40° C to obtain 25 g selective adsorbents containing bentonite dispersed in crosslinked dextrin polymer gels (particle sizes: 150 to 1200μ).

EXAMPLE 9

Thirty (30) grams of dextrin are swelled with 10 ml of water and then dissolved in 30 ml 5N-NaOH. Into this solution is dispersed homogeneously 10 g ground powders of Amberlite CG-50 (trade name: Organo Co.). The dispersion thus prepared is dispersed in fine droplets under stirring into 300 ml fluid paraffin of Japanese Pharmacopoeia containing 1% Lanex. Then 25 ml epichlorohydrin is added, dropwise, into this dispersion and stirring is continued at 50° C for 2 hours to obtain selective adsorbents. They are washed thoroughly with n-hexane, acetone, 1N-HCl and water, in this order, and dried on air stream at 40° C to obtain 40 g selective adsorbents containing ion-exchange resin powders dispersed in crosslinked dextrin polymer gels (particle sizes: 150 to 1000μ).

EXAMPLE 10

Twenty (20) grams of dextrin are swelled with 15 ml water and then dissolved in 25 ml 5N-NaOH. Into this solution is dispersed homogeneously 5 g alumina powders (produced by Merck Co.). The dispersion thus prepared is dispersed in fine droplets under stirring into 200 ml fluid paraffin of Japanese Pharmacopoeia containing 1% Lanex and then 20 ml epichlorohydrin is added, dropwise, to the dispersion. Stirring is continued at 50° C for one and half hours until selective adsorbents are obtained. They are separated by filtration, washed thoroughly with n-hexane, acetone and water, in this order and dried on air stream at 40° C to obtain 23 g selective adsorbents (particle sizes: 100 to 1000μ) containing alumina dispersed in crosslinked dextrin polymer gels.

EXAMPLE 11

Five (5) grams of agar powders (produced by Iwai Kagaku Yakuhin Co.) are dissolved in 100 ml water under heating at 60° C. Into this solution is added 6 g sodium hydroxide. Furthermore, 5 g activated charcoal powders (Kyoryoku Shirasagi) is dispersed homogeneously into this solution. The resulting activated charcoal dispersion is dispersed in fine droplets into 300 ml fluid paraffin of Japanese Pharmacopoeia (19 cps. at 25° C) containing 1% Lanex which is heated to 60° C under stirring with a propeller at 350 r.p.m. Then, 25 ml epichlorohydrin is added, dropwise, into this dispersion and stirring is continued at 60° C for 2 hours until selective adsorbents containing activated charcoal dispersed in crosslinked polymer gels of agar powders. They are separated by filtration, washed with n-hexane, acetone, water and 1N-HCl. They are further washed with water until they are neutralized to obtain 8 g (dry) selective adsorbents containing activated charcoal (particle sizes: 50 to 500μ).

EXAMPLE 12

Ten (10) grams of Agarose A-45 (trade name: produced by Seikagaku Kogyo Co.) are dissolved by 12 g sodium hydroxide and 120 ml water and 5 g activated charcoal is dispersed in the solution. The dispersion obtained is dispersed in fine droplets into 300 ml fluid paraffin of Japanese Pharmacopoeia (19 cps. at 25° C) containing 1% Lanex under stirring with a propeller at 350 r.p.m. Into this dispersion is further added, dropwise, 30 ml epichlorohydrin and stirring is continued at 50° C for 2 hours to obtain selective adsorbents containing activated charcoal dispersed in crosslinked polymer gels of agarose. They are separated by filtration, washed with n-hexane, acetone and 1N-HCl. They are further washed until they are neutralized and then dried on air stream at 40° C to obtain 13 g selective adsorbents containing activated charcoal (particle sizes: 30 to 200μ).

EXAMPLE 13

Into 500 ml of an aqueous 3% sodium carboxymethyl cellulose are dissolved 200 g acrylamide, 12 g N,N'-methylene-bis-acrylamide and 20 g ammonium persulfate, and then 30 g activated charcoal (Kyoryoku Shirasagi) is dispersed into this solution. The dispersion thus prepared is dispersed in fine droplets at room temperature under stirring into 3200 ml fluid paraffin containing 1% Lanex, having 15 ml N,N,N',N'-tetramethylene diethylamine dissolved therein. Stirring is continued under this state for about 3 hours until selective adsorbents having activated charcoal dispersed in three-dimensional spaces among gelled high molecular weight polymers. They are separated by filtration, washed with n-hexane, acetone and water, and dried under vacuum at 50° to 60° C to obtain 185 g selective adsorbents containing activated charcoal with sizes of 50 to 800μ.

EXAMPLE 14

Into 50 ml of an aqueous 3% sodium carboxymethyl cellulose solution are dissolved 20 g acrylamide, 1.5 g N,N'-methylene-bis-acrylamide and 2 g ammonium persulfate, and then 5 g activated charcoal (Kyoryoku Shirasagi) is dispersed into this solution. The dispersion obtained is dissolved in fine droplets at room temperature under stirring in 300 ml toluene containing 12 g ethylene-vinyl acetate copolymer (Ulthracene: trade name; produced by Toyo Soda Co.), having 2 ml 3-dimethyl aminopropyl nitrile dissolved therein. Stirring is continued under this state for about 3 hours. The gel-like substance precipitated is collected and washed to obtain 16 g selective adsorbents (particle sizes: 50 to 1000μ) having activated charcoal dispersed in three-dimensional spaces in high molecular weight polymers.

EXAMPLE 15

Into 50 ml of an aqueous 3% sodium carboxymethyl cellulose are dissolved 20 g acrylamide, 1.2 g N,N'-methylene-bis-acrylamide and 2 g ammonium persulfate, and 3 g ion-exchange resin powders (Amberlite IRC-50: trade name; produced by Rohm & Haas Co.) are dispersed into this solution. The dispersion is dispersed in fine droplets at room temperature under stirring into 300 ml fluid paraffin containing 1% Lanex, having 1.5 ml N,N,N',N'-tetramethylene diethylamine dissolved therein. Stirring is further continued for about 3 hours. The gel-like substance precipitated is recovered, and washed to obtain 17 g selective adsorbents having Amberlite IRC-50 powders in three-dimensional spaces in high molecular weight crosslinked polymers (sizes: 50 to 800μ).

EXAMPLE 16

Into 50 ml of an aqueous 2% sodium alginate solution are dissolved 20 g acrylamide 1.29 N,N'-methylene-bis-acrylamide and 0.8 g potassium persulfate, and then 3 g bentonite powders are dispersed into this solution. The dispersion thus prepared is dispersed in fine droplets at room temperature under stirring in 300 ml fluid paraffin containing 1% Lanex, having 1.5 ml N,N,N',N'-tetramethylene diethylamine dissolved therein. Stirring is further continued for about 3 hours. The gel-like substance precipitated is recovered and washed to obtain 18 g selective adsorbents having bentonite powders dispersed in three-dimensional spaces in high molecular weight polymer (sizes: 100 to 800μ).

EXAMPLE 17

Into 50 ml of an aqueous 3% sodium carboxymethyl cellulose solution are dissolved 20 g acrylamide, 1.2 g N,N'-methylene-bis-acrylamide and 2 g ammonium persulfate, and then 5 g ion-exchange resin powders (Amberlite IR-45: trade name; produced by Rohm & Haas Co.) are dispersed into this solution. The dispersion obtained is dispersed in fine droplets at room temperature under stirring into 300 ml fluid paraffin containing 1% Lanex, having 2 ml N,N,N',N'-tetramethylene diethylamine dissolved therein. Stirring is continued under this state for about 3 hours. The gel-like substance precipitated is recovered and washed to obtain 19 g selective adsorbents having Amberlite IR-45 powders dispersed in three-dimensional spaces in high molecular weight polymer (sizes: 50 to 800μ).

EXAMPLE 18

Into 50 ml water are dissolved 20 g acrylamide and 2 g ammonium persulfate, and then 2 g activated charcoal (Kyoryoku Shirasagi) is dispersed into this solution. After the dispersion is made acidic with HCl, 3 g of 40% glyoxal (produced by Wako Junyaku Kogyo Co.) is dissolved therein. The solution is dispersed in fine droplets under stirring into 300 ml fluid paraffin containing 1% Lanex. Stirring is then continued at 80° C for 3 hours. The gel-like substance precipitated is recovered and washed to obtain 18 g selective adsorbents with particle sizes of 50 to 800μ having activated charcoal dispersed in three-dimensional spaces in high molecular weight polymer.

EXAMPLE 19

Into 10 ml mixed solvent of toluene-t-amyl alcohol (1 : 1) are dissolved 12 g vinyl ethyl ether, 10 g technical divinyl benzene (containing 55% divinyl benzene in mixed solvent of ethyl vinyl benzene and ethyl benzene; produced by Tokyo Kasei Kogyo Co.) and 2 g benzoyl peroxide, and then 1 g activated charcoal is dispersed into this solution. The dispersion obtained is dispersed in fine droplets under stirring at 80° C into a solution of 200 mg sodium lauryl benzene sulfonate dissolved in 400 ml water. Stirring is continued under this state for 5 hours. The precipitated gel-like substance is recovered and washed to obtain 15 g selective adsorbents having activated charcoal dispersed in three-dimensional spaces in high molecular weight polymer (sizes: 80 to 800μ).

EXAMPLE 20

Into 20 ml of a mixed solvent of monochlorobenzene-t-amyl alcohol (1 : 1) are dissolved 12 g n-butyl methacrylate, 8 g of the same divinyl benzene as used in Example 19 and 2 g benzoyl peroxide, and then 2 g alumina powders are dispersed into this solution. The dispersion thus prepared is dispersed in fine droplets under stirring at 80° C into 400 ml water containing 0.2 g sodium lauryl benzene sulfonate. Stirring is continued under this state for about 5 hours. The gel-like substance precipitated is recovered and washed to obtain 14 g selective adsorbents with sizes of 80 to 1,000μ having alumina powders dispersed in three-dimensional spaces in high molecular weight polymer.

EXAMPLE 21

Into 10 ml mixed solvent of toluene-isoamyl alcohol (1 : 1) are dissolved 12 g styrene, 8 g of the same divinyl benzene as used in Example 19 and 2 g benzoyl peroxide, and then 2 g activated charcoal (Kyoryoku Shirasagi) is dispersed into this solution. The dispersion thus prepared is dispersed in fine droplets under stirring at 80° C into a solution of 0.2 g sodium lauryl benzene sulfonate dissolved in 400 ml water, and stirring is continued for 5 hours. The gel-like substance precipitated is recovered and washed to obtain 15 g selective adsorbents with sizes of 80 to 1,000μ having activated charcoal dispersed in three-dimensional spaces in high molecular weight polymer.

EXAMPLE 22

Into 250 ml aqueous 3% sodium carboxymethyl cellulose solution are dissolved 100 g acrylamide, 6 g N,N'-methylene-bis-acrylamide and 10 g ammonium persulfate, and then 60 g activated charcoal (Carborafin: trade name; produced by Takeda Chemical Industries Co.) is dispersed into this solution. The dispersion thus prepared is dispersed in fine droplets under stirring at room temperature into 1500 ml fluid paraffin containing 1% Lanex, having 7.5 ml N,N,N',N'-tetramethylene diamine. Stirring is continued under this state for about 3 hours to obtain selective adsorbents having activated charcoal powders dispersed in three-dimensional spaces in gelled high molecular weight polymer. They are separated by filtration, washed with n-hexane, acetone and water, and then dried to obtain 90 g selective adsorbents with sizes of 80 to 750μ containing activated charcoal.

EXAMPLE 23

A simulated kanamycin culture broth is prepared by sterilizing 160 ml glucose-bouillon medium under heating at 120° C for 15 minutes and adding kanamycin sulfate with 60 mg activity thereto. Then, the solution is passed through a column, 2 cm in diameter, wherein 6 g (dry weight) selective adsorbents containing activated charcoal as obtained in Example 1, after being sufficiently swelled with water, are packed, at the rate of 0.5 ml/minute. The column is then washed and further eluted with 0.1N HCl-methanol (1 : 1). Active fractions are combined, wherefrom kanamycin with 54 mg activity (90% recovery) is obtained in high purity and high yield (decoloration degree: 99%; purity: 98%).

EXAMPLE 24

A medium (pH 7.0), 100 ml, containing 1% starch, 1% wasted molasses, 1% peptone and 1% meat extract is charged into 500 ml Sakaguchi's flask and sterilized at 120° C for 30 minutes. Into this medium is inoculated *Streptomyces glyzeobarchsiratus parietus tuberacticus* No. N 6-130 (FERM-P No. 615 deposited at Institute of Fermentation Research, Japan) and culturing is performed by a reciprocating culturing shaker with stroke of 7 cm and frequency of 130/minute at 30° C for 2 days. The culture broth, 400 ml, is inoculated aseptically into a culture medium which is prepared by adding 5 ml defoaming agent (Uniol D-2000: trade name; produced by Nihon Yushi Co.) to 20 liter of a medium containing 1% starch, 1% wasted molasses, 1% peptone and 1% meat extract and sterilizing the medium in a 30 liter jar fermenter at 120° C for 30 minutes. Cultivation is continued at 30° C for 92 hours at 200 r.p.m. while blowing sterilized air at the rate of 20 liter/ minute, whereby is obtained 19 liter of culture broth containing 2260 mcg/ml of tuberactinomycin N. Then, solid components are removed from this culture broth and 50 ml of the resulting clear fluid is treated through a column, 2 cm in diameter, wherein 6 g of the selective adsorbents (dry weight) as obtained in Example 3 are packed, at the rate of 0.5 ml/minute. After washing with water, the column is eluted with 0.1N-HCl, whereby tuberactinomycin N hydrochloride is obtained in the eluate without elution of colored substance. The eluate is neutralized with sodium hydroxide and thereafter concentrated under reduced pressure to 2 ml, while removing by filtration sodium chloride precipitated. To the concentrate is added 14 ml methanol and the precipitates formed after standing at 5° C overnight are separated by filtration. They are washed with methanol, and dried under reduced pressure to obtain 82 g crude product of tuberactinomycin (yield: 69%; purity: 95%).

EXAMPLE 25

To 25 ml egg white obtained from a hen's egg is added 75 ml water and the mixture is homogenized at 10,000 r.p.m. for 5 minutes. From the homogenate is taken 15 ml aqueous egg white solution and 30 ml water is further added thereto to prepare 45 ml lysozyme containing solution. Separately, 3 g (dry weight) of the selective adsorbents containing activated charcoal as obtained in Example 2 are packed in a column of 1 cm in diameter. Then, a portion of the lysozyme containing solution, 20 ml, is charged into this column under the flowing condition of 0.25 ml/minute. The column is washed with 50 ml water and the effluent is collected by fraction collector in each 5 ml. Subsequently, said column is eluted with 0.1N-HCl at the rate of 25 ml/minute and the eluate is collected by fraction collector in each 10 ml. The eluate fraction No. 1 is combined with the aforesaid effluent (hereinafter referred to as eluate fraction No. 1 +). The eluate fractions No. 2 to No. 4 are admixed with 1 ml 0.01 mol tris-buffer solution (pH 8.0) and 1 ml 1N sodium hydroxide, respectively, and absorbance of each mixture at 280 m$\mu$ is measured by a spectrophotometer. Furthermore, 0.5 ml of each of the aforesaid fractions is added to 4.5 ml suspension ($OD_{540\ m\mu}$ = 0.760) of *Micrococcus lysodeikticus* ATCC 4698 strain suspended in 0.01 mol phosphate buffer solution (pH 6.24) and the reaction is carried out at 37° C. Reduction in turbidity in each reaction mixture is measured by a spectrophotometer. The results are set forth in Table 1, wherein Control is the remaining solution, 20 ml, of the lysozyme containing solution as prepared above.

Table 1

| Fraction No. | Amount of liquid | $OD_{280m\mu}$ | Lysozyme activity | Specific activity |
|---|---|---|---|---|
| Control | 20 ml | 7.10 | 150,000 U | 1.055 U/mg |
| No. 1 + | 80 ml | 1.65 | 0 | 0 |
| No. 2 | 12 ml | 0.10 | 30,000 U | 23,000 |
| No. 3 | 12 ml | 0.30 | 90,000 U | U/mg |
| No. 4 | 12 ml | 0.11 | 25,000 U | (average) |

As shown in the above results, no lysozyme activity is detected at all in fraction No. 1 + but other proteins than lysozyme (e.g. ovalbumin) are found to be contained therein. The sum of lysozyme activities of fractions No. 2 to 4 is 145,000 U, which shows that, as compared with Control, about 97% thereof is collected. Furthermore, the specific activity of the fractions No. 2 to 4 (average) is found to be 23,800 U/mg, which is by far superior in purity to commercially available lysozyme crystals (trade name: Lysozyme; produced by Sigma Co.) which has a specific activity of 25,000 U/mg. These fractions No. 2 to 4 are combined and lyophilized to obtain 130 mg lysozyme (purity: 97%; yield: 89%).

EXAMPLE 26

An aqueous solution ($OD_{280\ m\mu}$: 98.49) of 20 mg cytochrome C (produced by Myrus Sebarac Co.) dissolved in 10 ml water is passed at the rate of 0.5 ml/minute through a column, 1.5 cm in diameter, wherein 3 g (dry weight) selective adsorbents containing Amberlite CG-50 as obtained in Example 9 are packed. When the effluent is subjected to measurement at $OD_{280\ m\mu}$, it is found that 100% cytochrome C is adsorbed. Through the column is then passed 15% ammonium sulfate solution at the rate of 0.5 ml/minute and 14 fractions are collected in each 5 ml by fraction collector. Each eluate is measured at $OD_{280\ m\mu}$ Table 2

| Fraction No. | $OD_{280\ m\mu}$ value |
|---|---|
| 1 | 0 |
| 2 | 7.170 |
| 3 | 21.950 |
| 4 | 17.500 |

Table 2-continued

| Fraction No. | $OD_{280\ m\mu}$ value |
|---|---|
| 5 | 12.215 |
| 6 | 9.725 |
| 7 | 7.375 |
| 8 | 5.780 |
| 9 | 4.200 |
| 10 | 3.750 |
| 11 | 3.125 |
| 12 | 2.350 |
| 13 | 1.050 |
| 14 | 0.740 |

As the result, absorbance of cytochrome C is observed in fractions No. 2 to 14. Said fractions are combined and lyophilized to recover 19.6 mg cytochrome C (98.4% recovery percentage).

EXAMPLE 27

A solution similar to kanamycin culture broth is prepared by sterilizing 160 ml glucose-bouillon medium under heating at 120° C for 15 minutes and, after cooling, adding 80 mg kanamycin sulfate thereto. Then, the solution is passed through a column, 1.5 cm in diameter, wherein 30 g selective adsorbents as obtained in Example 13 are packed, at the rate of 0.5 ml/minute. The column is thereafter washed with water and further eluted with 0.01N-HCl-methanol (1 : 1). Active fractions are combined to provide kanamycin hydrochloride with 75.5 mg activity, decoloration degree of 97% and purity of 95%.

EXAMPLE 28

A solution obtained by dissolving 10 mg alkali phosphatase (molecular weight: about 100,000; produced by Seikagaku Kogyo Co.) in 10 ml aqueous 0.1% crystal violet solution ($OD_{590\ m\mu}$: 5.2) is passed at the rate of 0.5 ml/minute through a column, 1.5 cm in diameter, wherein the selective adsorbents as obtained in Example 14 are packed. The effluent is collected and measured at $OD_{590\ m\mu}$ to obtain the result that it is decolorized with good efficiency, namely, with decoloration degree as much as 99%. Furthermore, 0.5 ml of said effluent is added to a mixture of 0.2 ml of 0.01 mol paranitrophenyl phosphate, 1 ml of 0.1 mol borate buffer solution (pH 9.0) and 0.3 ml water and the reaction is performed at 37° C for 10 minutes. The reaction mixture, after addition of 1 ml of 0.5N sodium hydroxide, is measured at $OD_{420\ m\mu}$ to find that recovery percentage of alkali phosphatase 97%.

EXAMPLE 29

The clear fluid, 50 ml, of the culture broth filtrate of tuberactinomycin-N obtained in Example 24 is passed through a column, 2 cm in diameter, wherein 8 g selective adsorbents obtained in Example 24 are packed, at the rate of 0.5 ml/minute. After the column is further washed with water, it is eluted with 0.1N-HCl to obtain decolored aqueous solution containing tuberactinomycin-N. The aqueous solution is neutralized with sodium hydroxide and then concentrated under reduced pressure, while removing by filtration sodium chloride precipitated, until it is concentrated to about 2 ml. To the resulting concentrate is added 15 ml methanol. The precipitate formed after standing overnight is collected by filtration and, after washing with methanol, dried under reduced pressure to obtain 91 mg crude product of tuberactinomycin-N (purity: 93%; yield: 76.6%).

EXAMPLE 30

A waste liquor of yeast fermentation (pH 5.4), 1000 ml, is adjusted to pH 3.8 with HCl and solid components are removed therefrom by centrifugation to provide a clear fluid. Then, this solution ($OD_{420\ m\mu} = 28.0$) is charged at the rate of 1 ml/minute through a column (2 cm × 33 cm) wherein 90 g selective adsorbents obtained in Example 22 are packed. After the total amount is charged, the column is washed with water and then eluted with 0.25N aqueous ammonia at the rate of 0.5 ml/minute to provide eluate colored in dark brown at the rate of 0.5 ml/minute in fractions of each 10 ml. The fractions No. 10 to 20 are combined (pH 6.8; $OD_{420\ m\mu} = 120.0$; liquid volume: 100 ml) and concentrated under reduced pressure at about 45° C to 20 ml to obtain caramel dyestuff solution (solid content: 3.1 g).

EXAMPLE 31

In this Example, adsorption ability for Methylene Blue of some selective adsorbents obtained in the above Examples are compared with that of several Controls. As Controls, activated charcoal (trade name: Kyoryoku Shirasagi; produced by Takeda Chemical Industries Co.; Control 1), a commercially available granular activated charcoal (trade name: Adoster B 1-L; produced by Ados Kasei Co.; Control 2) and another commercially available granular activated charcoal (trade name: Adoster P 5-L; produced by Ados Kasei Co.; Control 3) are used. The amounts used all correspond to 1 g powdery adsorbents. Adsorption ability is measured by the method wherein each of selective adsorbents and Controls is added to 100 ml of 0.01% Methylene Blue ($OD_{595\ m\mu} = 5.500$) or 0.005% Methylene Blue ($OD_{595\ m\mu} = 2.70$), mixed, left to stand overnight, followed by filtration, and the filtrate is measured at $OD_{595\ m\mu}$.

Table 3

| Sample | (0.01% Methylene Blue) | |
|---|---|---|
| | Absorbance | Adsorption degree |
| Control 1 | 0 | 100 |
| Example 1 | 0.021 | 99.6 |
| Example 2 | 0.106 | 98.1 |
| Example 3 | 0.088 | 98.4 |
| Control 2 | 1.900 | 65.5 |
| Control 3 | 1.852 | 66.4 |

Table 4

| Sample | (0.005% Methylene Blue) | |
|---|---|---|
| | Absorbance | Adsorption degree |
| Control 1 | 0 | 100 |
| Example 13 | 0.041 | 98 |
| Example 14 | 0.220 | 92 |
| Example 18 | 0.360 | 87 |
| Control 2 | 1.11 | 59 |
| Control 3 | 0.645 | 76 |

Note
Adsorption degree =

$$\frac{\left(\begin{array}{c}\text{OD value of}\\ \text{Methylene Blue}\end{array}\right) - \left(\begin{array}{c}\text{OD value of}\\ \text{filtrate}\end{array}\right)}{(\text{OD value of Methylene Blue})} \times 100\ (\%)$$

As the result, adsorption ability for Methylene Blue of the selective adsorbents obtained in Examples 1, 2 3, 13, 14 and 18 is substantially the same as that of untreated activated charcoal of Control 1 and by far superior over that of commercially available products of Controls 2 and 3.

EXAMPLE 32

Adsorption ability of the selective adsorbents obtained in Example 4 is compared with that of untreated activated charcoal by using antibiotic substance tuberactinomycin-N (molecular weight: 798) as substrate. As the result, while untreated activated charcoal is capable of adsorbing 110 mg tuberactinomycin-N per 420 mg, the selective adsorbents obtained in Example 4 are capable of adsorbing 105 mg tuberactinomycin-N per 3.5 g (containing 420 mg activated charcoal); adsorption degree being 95.5% as compared with that of untreated activated charcoal which is 100.

EXAMPLE 33

When adsorption ability is measured for the selective adsorbents obtained in Examples 4, 8 and 9 together with corresponding untreated activated charcoal, bentonite and Amberlite CG-50 by using lysozyme (molecular weight: 14,000), the results as shown in Table 5 are obtained. It can be seen from Table 5 that adsorption ability is increased for lysozyme by making activated charcoal or bentonite into selective adsorbents. Particularly, in selective adsorbents containing activated charcoal, the increase in adsorption ability is found to be conspicuous when adsorption is effected by column method.

Table 5

| Adsorbent | Amount of lysozyme adsorbed (mg) | Relative adsorption ability |
|---|---|---|
| Activated charcoal powder (420 mg) | 122 | 100 |
| Example 4 (corresponding to 420 mg) | 150 | 123 |
| Example 4* (corresponding to 420 mg) | 409 | 336 |
| Bentonite (300 mg) | 202 | 100 |
| Example 8 (corresponding to 300 mg) | 234 | 116 |
| Amberlite CG-50 (300 mg) | 181 | 100 |
| Example 9 (corresponding to 300 mg) | 124 | 68 |

Note) The amount of lysozyme adsorbed is determined by introducing each sample in 1 liter of 0.5 mg/ml aqueous lysozome solution and, after 48 hours, measuring the filtrate at $OD_{280\ m\mu}$. Exceptionally, the sample marked with asterisk is packed in a column of 1 cm in diameter, the above lysozyme solution is passed therethrough and the amount adsorbed is determined from $OD_{280\ m\mu}$ values of respective fractions.

EXAMPLE 34

Adsorption ability of the selective adsorbents obtained in Examples 16 and 20 for riboflavin is measured. As Controls, bentonite powders (produced by Kukita Yakuhin Kogyo Co.) and alumina powders (produced by Wako Junyaku Kogyo Co.) are used. The amounts used all correspond to 1 g adsorbent powder. Adsorption ability is measured according to the method wherein each of the above selective adsorbents and Controls is added to 100 ml aqueous riboflavin solution ($OD_{450\ m\mu}$: 0.885), mixed and the mixture is left to stand for 24 hours, followed by filtration. Adsorption ability for riboflavin is determined by measurement of the filtrate at $OD_{450\ m\mu}$.

Table 6

| | Absorbance | Adsorption degree |
|---|---|---|
| Bentonite powders | 0.150 | 83 |
| Alumina powders | 0.220 | 75 |
| Example 16 | 0.180 | 80 |

Table 6-continued

| | Adsorbance | Adsorption degree |
|---|---|---|
| Example 20 | 0.265 | 70 |

Note)
$$\text{Adsorption degree} = \frac{0.885 - (\text{Absorbance of filtrate})}{0.885} \times 100 \, (\%)$$

As the result, as shown in Table 6, the selective adsorbents of the present invention are not substantially deteriorated in adsorption ability in comparison with Controls.

EXAMPLE 35

This Example illustrates selective adsorbing effect of the selective adsorbents obtained in Examples 1 through 7, 13, 14, 18 and 19. Samples used for measurement of selective adsorbing effect are as follows:

| Samples | Molecular weight |
|---|---|
| A : Methylene Blue | 374 |
| B : Tuberactinomycin N | 798 |
| C : Polymyxin B | 1280 |
| D : Insulin | 5700 |
| E : Egg white lysozyme | 14000 |
| F : α-Chymotrypsin | 24500 |
| G : Semialkali protease | 30000 |
| H : Pepsin | 35000 |
| I : Ovalbumin | 45000 |
| J : Serum alubumin | 67000 |
| K : γ-Globulin | 156000 |

Measurements are carried out by packing selective adsorbents of each Example (in amount corresponding to 1 g adsorbent powders) in a column of 1 cm in diameter and flowing out aqueous solutions of the above Samples (A through K) dissolved in 10 ml of water at the rate of 0.5 ml/minute, respectively, followed by thorough washing with water. Then, the effluent and the washed liquid recovered are subjected to measurement. In Sample A, measurements are performed at $OD_{595 \, m\mu}$. In Sample C, anti-bacterial resistance is measured by 8 mm paper disc method by using *Pseudomonas aeruginosa* $A_3$ as test organism. In other Samples, measurements are performed at $OD_{280 \, m\mu}$. The sum of the values multiplied by the liquid amount is compared with absorbance of each sample to determine adsorption degree.

Table 7

| Sample (concentration) | Adsorption degree (%) | | | | | | | | | | |
|---|---|---|---|---|---|---|---|---|---|---|---|
| | Example 1 | Example 2 | Example 3 | Example 4 | Example 5 | Example 6 | Example 7 | Example 13 | Example 14 | Example 18 | Example 19 |
| Sample A(5mg/ml) | 100 | 100 | 100 | 100 | 100 | 100 | 100 | — | — | — | — |
| " A(1 ") | — | — | — | — | — | — | — | 100 | — | 100 | — |
| " A(0.5 ") | — | — | — | — | — | — | — | — | 100 | — | 100 |
| " B(10 ") | 100 | 100 | 100 | 100 | 100 | 100 | 100 | — | — | — | — |
| " B(3 ") | — | — | — | — | — | — | — | 100 | — | 100 | — |
| " B(1.5 ") | — | — | — | — | — | — | — | — | 100 | — | 100 |
| " C(0.5 ") | 100 | 100 | 100 | 100 | 100 | 100 | 100 | — | — | — | — |
| " D(5 ") | 100 | 100 | 100 | 100 | 100 | 100 | 100 | — | — | — | — |
| " D(2 ") | — | — | — | — | — | — | — | 100 | — | 100 | — |
| " D(1 ") | — | — | — | — | — | — | — | — | 100 | — | 100 |
| " E(3 ") | — | — | — | — | — | — | — | 97 | — | 92 | — |
| " E(2.5 ") | 100 | 100 | 95 | 96 | 93 | 70 | 100 | — | — | — | — |
| " E(1.5 ") | — | — | — | — | — | — | — | — | 95 | — | 90 |
| " F(10 ") | 97 | 94 | 84 | 13 | 9 | 10 | 48 | — | — | — | — |
| " F(3 ") | — | — | — | — | — | — | — | 88 | — | 72 | — |
| " F(1.5 ") | — | — | — | — | — | — | — | — | 85 | — | 25 |
| " G(10 ") | 86 | 55 | 10 | 7 | 0 | 0 | 15 | — | — | — | — |
| " G(3 ") | — | — | — | — | — | — | — | 10 | — | 15 | — |
| " G(1.5 ") | — | — | — | — | — | — | — | — | 12 | — | 10 |
| " H(5 ") | 33 | 15 | 0 | 0 | 0 | 0 | 0 | — | — | — | — |
| " H(3 ") | — | — | — | — | — | — | — | 8 | — | 10 | — |
| " H(1.5 ") | — | — | — | — | — | — | — | — | 5 | — | 4 |
| " I(10 ") | 0 | 0 | 0 | 0 | 0 | 0 | 0 | — | — | — | — |
| " I(3 ") | — | — | — | — | — | — | — | 0 | — | 0 | — |
| " I(1.5 ") | — | — | — | — | — | — | — | — | 0 | — | 0 |
| " J(10 ") | 0 | 0 | 0 | 0 | 0 | 0 | 0 | — | — | — | — |
| " J(3 ") | — | — | — | — | — | — | — | 0 | — | 0 | — |
| " J(1.5 ") | — | — | — | — | — | — | — | — | 0 | — | 0 |
| " K(10 ") | 0 | 0 | 0 | 0 | 0 | 0 | 0 | — | — | — | — |
| " K(3 ") | — | — | — | — | — | — | — | 0 | — | 0 | — |
| " K(1.5 ") | — | — | — | — | — | — | — | — | 0 | — | 0 |

As clearly seen from the results set forth in Table 7, the selective adsorbents exhibit selective adsorption for organic compounds within specific molecular weight range and therefore can function as molecular sieving particles.

The adsorptive organic compounds and nonadsorptive compounds may be determined exemplarily from the results in Table 7 in the following manner. The term "adsorptive organic compound" used in the specification and claims refers to an organic compound which can be adsorbed by the selective adsorbents of the present invention in an effective amount. The effective amount is not absolute but relative with the value of the organic compound and the object of separation. For example, effective amount is defined with reference to the amount of adsorption which is required to fulfill the object of separation or purification of organic compounds contained in a solution or with reference to the amount obtained when adsorbed organic compounds are eluted, if said amount is yet valuable. For example, if the adsorptive organic compounds are defined as the organic compounds having adsorption degree of about 50% or more, and the non-adsorptive organic compounds as the organic compounds having adsorption degree of at most about 10%, the adsorptive and nonadsorptive organic compounds for the selective adsorbents of the above Examples have the following molecular weight ranges, respectively:

Table 8

| Selective adsorbent | | Molecular weight of adsorptive organic compounds | | Molecular weight of non-adsorptive organic compounds | |
|---|---|---|---|---|---|
| Example | 1 | 33000 | or less | 42000 | or more |
| " | 2 | 30000 | " | 38000 | " |
| " | 3 | 27000 | " | 30000 | " |
| " | 4 | 20000 | " | 26000 | " |
| " | 5 | 20000 | " | 24000 | " |
| " | 6 | 18000 | " | 23000 | " |
| " | 7 | 24000 | " | 29000 | " |
| " | 13 | 27000 | " | 30000 | " |
| " | 14 | 28000 | " | 31000 | " |
| " | 18 | 27000 | " | 31000 | " |
| " | 19 | 21000 | " | 30000 | " |

Thus the selective adsorbents obtained in Examples 1 through 7, 13, 14, 18 and 19 have respective specific molecular sieving effect in the molecular weight ranges as listed above. Furthermore, the selective adsorbents according to the present invention can have specific molecular sieving effect in the molecular ranges lower or higher than in the above Examples. For example, molecular sieving effect may be in the range of molecular weight of 1000 to 1500 which is suitable for molecular sieving separation of low molecular weight organic compounds. Alternatively, it may be in the range of 50,000 to 60,000, which is suitable for molecular sieving separation of higher molecular weight organic compounds.

EXAMPLE 36

Comparative tests are made for separation and purification by using the selective adsorbent of Example 4, activated charcoal and dextran gel. First, activated charcoal (Shirasagi: carbon for chromatography; produced by Takeda Chemical Industries Co.) is packed in a column and a kanamycin culture broth is charged therethrough. Kanamycin can thereby be adsorbed even in dilute solution, but high molecular weight adsorbable substances such as polypeptide or high molecular weight dyestuff are also adsorbed at the same time. Therefore, when kanamycin is eluted with 0.01N-HCl-methanol (1 : 1) mixture, these components are also eluted together therewith; the eluate contains colored substances and purity of kanamycin is not good (purity: 89%). When similar test is performed for activated charcoal larger in mesh size which is suitable for industrially advantageous continuous column operation, said activated charcoal is found to be inferior in adsorption ability for kanamycin to that of activated charcoal powders. Then, separation and purification are tested by packing dextran gel (Sephadex G-10; produced by Seikagaku Kogyo Co.) in a column. Because Sephadex has only molecular sieving effect, separation of components having molecular weights near to kanamycin, for example, low molecular weight peptide or glucose, is difficult. In separation and purification by the use of this Sephadex, a large amount of culture broth cannot be treated. When the amount charged is increased, higher molecular weight substances are mixed in kanamycin fraction to provide kanamycin with low purity. On the other hand, when the selective adsorbent obtained in Example 4 is used, only substances, which have molecular weight of 20000 or less and are adsorbable by activated charcoal, are captured in a column, other higher molecular weight substances as well as low molecular weight substance not adsorbable by activated charcoal such as glucose being passed through said column. Accordingly, when elution is performed with 0.01N HCl-methanol (1 : 1) mixture, kanamycin fraction contains little impurity to provide high purity product (97% or more). Furthermore, even when a large amount of culture broth is passed through the column, kanamycin concentration can be enhanced in the eluate, because the selective adsorbent is so high in adsorption ability that kanamycin is adsorbed in particularly high concentration.

What we claim is:

1. A selective adsorbent shaped in the form of spherical particles having sizes of 30 to 1200μ, each particle containing fine powders of an adsorbent with particle sizes of 0.5 to 50μ dispersed in a matrix of a crosslinked polymer, said selective adsorbent being produced by a process comprising dispersing an adsorbent in the form of a fine powder in a composition for forming a crosslinked polymer containing a mixture selected from the group consisting of (a) a mixture of hydroxyl group-containing polymeric substance and a polyfunctional crosslinking agent reactive with hydroxyl groups and (b) a monomeric mixture of an ethylenically unsaturated monomer and a polyfunctional crosslinking monomer for said ethylenically unsaturated monomer to form a dispersion, dispersing said dispersion in the form of fine droplets in a vehicle, and effecting crosslinking to convert the fine droplets into spherical particles each comprising a crosslinked polymer matrix with said fine particles of the adsorbent dispersed therein.

2. A selective adsorbent as claimed in claim 1 wherein the composition for forming a crosslinked polymer contains a hydroxyl group containing polymeric substance and a polyfunctional crosslinking agent reactive with hydroxyl group.

3. A selective adsorbent as claimed in claim 1 wherein the composition for forming a crosslinked polymer is a monomeric mixture of an ethylenically unsaturated monomer and a polyfunctional crosslinking monomer.

4. A selective adsorbent according to claim 1 wherein said polymeric substance is selected from the group consisting of dextrin, dextran, starch, agar, agarose, cellulose, polyglucose, methyl dextran, ethyl dextran, hydroxypropyl dextran, methyl cellulose, ethyl cellulose, sorbitol and polyvinyl alcohols.

5. A selective adsorbent as claimed in claim 4, wherein said composition is composed of a solution, said adsorbent being dispersed in a solution of said polymeric substance and polyfunctional crosslinking agent in a solvent therefore.

6. A selective adsorbent as claimed in claim 5, wherein said vehicle is water immiscible.

7. A selective adsorbent as claimed in claim 6, wherein said solvent is water.

8. A selective adsorbent according to claim 6, wherein said crosslinking agent is selected from the group consisting of bis-epoxy-propylether, ethylene glycol-bis-epoxy-propyl ether, and 1,4-butane-diol-bis-epoxy-propyl ether.

9. A selective adsorbent as claimed in claim 6, wherein the amount of said polymeric substance containing hydroxyl groups in said composition is about 40 to 90% by weight and the amount of adsorbent in said composition is about 10 to 60% by weight, on a dry basis.

10. A selective adsorbent according to claim 9, wherein the amount of said vehicle is at least about three times as much as the amount of said solution.

11. A selective adsorbent as claimed in claim 10, wherein the amount of crosslinking agent in said composition is about one-third to one-half the amount of said polymeric substance on a weight basis.

12. A selective adsorbent as claimed in claim 6, wherein said composition contains a surfactant.

13. A selective adsorbent as claimed in claim 3, wherein said ethylenically unsaturated monomer is selected from the group consisting of vinyl chloride, vinyl acetate, vinyl ethyl ether, allyl, alcohol, allyl amine, styrene, butadiene, acrylic acid, methacrylic acid, crotonic acid, acrylamide, N-dimethyl acrylamide, dimethylamino styrene, vinyl sulfonic acid and mixtures thereof.

14. A specific adsorbent as claimed in claim 13, wherein said composition is a solution said adsorbent being dispersed in a solution of said ethylenically unsaturated monomer and said polyfunctional crosslinking monomer in a solvent therefor.

15. A selective adsorbent according to claim 14, wherein said ethylenically unsaturated monomer is hydrophilic, said vehicle being lipophilic.

16. A selective adsorbent as claimed in claim 14, wherein said ethylenically unsaturated monomer is lipophilic, said vehicle being hydrophilic.

17. A selective adsorbent as claimed in claim 14, wherein said crosslinking agent is selected from the group consisting of polyhydric alcohol esters of acrylic acid, methacrylic acid or crotonic acid, divinyl benzene, acrylic acid anhydride, methacrylic acid anhydride, N,N'-dimethylene-bis-acrylamide, glyoxal, ketones, allyl dihalogenides, alkyl dihalogenides, disulfohalogenides and polybasic acids.

18. A selective adsorbent as claimed in claim 18, wherein said crosslinking agent is selected from the group consisting of N,N'-dimethylene-bis-acrylamide, divinyl benzene and glyoxal.

19. A selective adsorbent as claimed in claim 14, wherein the amount of said crosslinking agent is 0.5 to 50% by weight based on the weight of the crosslinked polymer obtained.

20. A selective adsorbent as claimed in claim 19, wherein the concentration of the ethylenically unsaturated monomer dissolved in a solvent is at least 5% by weight.

21. A selective adsorbent as claimed in claim 20, wherein the amount of adsorbent in said solution is 60% by weight or less.

22. A selective adsorbent as claimed in claim 21, wherein the concentration of the ethylenically unsaturated monomer dissolved in said solvent is about 10 to 50% by weight, and further wherein the amount of adsorbent in said solution is about 10 to 30% by weight.

23. A selective adsorbent as claimed in claim 21, wherein the amount of said vehicle mixed with said composition is about three to five times the amount of said composition.

24. A selective adsorbent as claimed in claim 1, wherein said mixture for forming a crosslinked polymer is selected from the group consisting of (a) a mixture of a polymeric substance, selected from the group consisting of dextrin, dextran, starch, agar, agarose, cellulose, polyglucose, methyl dextran, ethyl dextran, hydroxylpropyl dextran, methyl cellulose, ethyl cellulose and sorbitol, and a polyfunctional crosslinking agent reactive with hydroxyl groups and (b) a monomeric mixture of an ethylenically unsaturated monomer, selected from the group consisting of vinyl chloride, vinyl acetate, vinyl ethyl ether, allyl alcohol, allyl amine, styrene, butadiene, acrylic acid, methacrylic acid, crotonic acid, acrylamide, N-dimethyl acrylamide, dimethylamino styrene, vinyl sulfonic acid and mixtures thereof, and a polyfunctional crosslinking monomer for said ethylenically unsaturated monomer.

25. A process for forming a selective adsorbent shaped in the form of spherical particles having sizes of 30 to 1200$\mu$, each particle composed of a crosslinked polymer matrix having an adsorbent in the form of fine powder with particle sizes of 0.5 to 50$\mu$ dispersed therein, said process comprising dispersing an adsorbent in the form of a fine powder in a composition for forming a crosslinked polymer, said composition being selected from the group consisting of (a) a solution of a hydroxyl group-containing polymeric substance and a polyfunctional crosslinking agent reactive with hydroxyl groups dissolved in a solvent therefor and (b) a solution of an ethylenically unsaturated monomer and a polyfunctional crosslinking monomer for crosslinking said ethylenically unsaturated monomer in a solvent therefor, dispersing the dispersion so obtained in the form of fine droplets in a vehicle, and effecting crosslinking to convert the fine droplets into spherical particles each comprising a polymer matrix containing adsorbent in the form of fine powder therein.

26. The process of claim 25, wherein said composition is a solution that contains a hydroxyl group containing polymeric substance and a polyfunctional crosslinking agent reactive with hydroxyl groups.

27. The process of claim 25, wherein said composition is a solution that contains an ethylenically unsaturated monomer and a polyfunctional crosslinking monomer.

28. The process of claim 25, wherein said composition for forming a crosslinked polymer comprises a mixture that is selected from the group consisting of (a) a mixture of a polymeric substance, selected from the group consisting of dextrin, dextran, starch, agar, agarose, cellulose, polyglucose, methyl dextran, ethyl dextran, hydroxylpropyl dextran, methyl cellulose, ethyl cellulose and sorbitol, and a polyfunctional crosslinking agent reactive with hydroxyl groups and (b) a monomeric mixture of an ethylenically unsaturated monomer, selected from the group consisting of vinyl chloride, vinyl acetate, vinyl ethyl ether, allyl alcohol, allyl amine, styrene, butadiene, acrylic acid, methacrylic acid, crotonic acid, acrylamide, N-dimethyl acrylamide, dimethylamino styrene, vinyl sulfonic acid and mixtures thereof, and a polyfunctional crosslinking monomer for said ethylenically unsaturated monomer.

29. A selective adsorbent shaped in the form of spherical particles having sizes of 30 to 1200$\mu$, each particle containing fine powders of an adsorbent with particle sizes of 0.5 to 50$\mu$ dispersed in a matrix of a crosslinked polymer, said selective adsorbent being produced by a process comprising dispersing an adsorbent in the form of a fine powder in a solution of a mixture of a polymeric substance selected from the group consisting of dextrin, dextran, starch, agar, agarose, cellulose, polyglucose, methyl dextran, ethyl dextran, hydroxylpropyl dextran, methyl cellulose, ethyl cellulose and sorbitol, and a polyfunctional crosslinking agent selected from the group consisting of epichlorohydrin, dichlorohydrin, 1,2,3,4-diepoxy butane, bis-epoxy-propylether ethylene glycol-bis-epoxy-propyl ether and 1,4-butanediol-bis-epoxy-propyl ether, dispersing the thus formed dispersion in the form of fine droplets in a vehicle, and effecting crosslinking to convert said fine droplets into spherical particles each comprising a crosslinked polymer matrix with said fine powders of the adsorbent dispersed therein.

30. A selective adsorbent shaped in the form of spherical particles having sizes of 30 to 1200μ, each particle containing fine powders of an adsorbent with particle sizes of 0.5 to 50μ dispersed in a matrix of a crosslinked polymer, said selective adsorbent being produced by a process comprising dispersing an adsorbent in the form of a fine powder in a solution of a mixture of an ethylenically unsaturated monomer selected from the group consisting of vinyl chloride, vinyl acetate, vinyl ethyl ether, allyl alcohol, allyl amine, styrene, butadiene, acrylic acid, methacrylic acid, crotonic acid, acrylamide, N-dimethyl acrylamide, dimethylamino styrene, vinyl sulfonic acid and mixtures thereof and a polyfunctional crosslinking monomer selected from the group consisting of polyhydric alcohol esters of acrylic acid, methacrylic acid or crotonic acid, divinyl benzene, acrylic acid anhydride, methacrylic acid anhydride, N,N'-dimethylene-bis-acrylamide, glyoxal, ketones, allyl dihalogenides, alkyl dihalogenides, disulfohalogenides and polybasic acids, dispersing the resulting dispersion in the form of fine droplets in a vehicle, and effecting crosslinking to convert the fine droplets into spherical particles within said vehicle each particle comprising a crosslinking polymer matrix with said fine powder of adsorbent dispersed therein.

* * * * *